(12) United States Patent  
Sanchez et al.

(10) Patent No.: US 11,892,361 B2  
(45) Date of Patent: Feb. 6, 2024

(54) DEVICE AND METHOD TO MEASURE TEMPERATURE DURING TRIBOLOGICAL EXAMINATION OF MATERIALS

(71) Applicant: SOUTHWEST RESEARCH INSTITUTE, San Antonio, TX (US)

(72) Inventors: Carlos Sanchez, San Antonio, TX (US); Michael Moneer, San Antonio, TX (US); Peter Lee, Fair Oaks Ranch, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 226 days.

(21) Appl. No.: 17/644,413

(22) Filed: Dec. 15, 2021

(65) Prior Publication Data

US 2022/0187141 A1 Jun. 16, 2022

Related U.S. Application Data

(60) Provisional application No. 63/126,182, filed on Dec. 16, 2020.

(51) Int. Cl.
| | |
|---|---|
| *G01K 7/02* | (2021.01) |
| *G01N 19/00* | (2006.01) |
| *G01K 1/14* | (2021.01) |
| *G01N 33/30* | (2006.01) |
| *G01N 19/02* | (2006.01) |

(52) U.S. Cl.  
CPC ............... *G01K 7/02* (2013.01); *G01N 19/00* (2013.01)

(58) Field of Classification Search  
CPC ............ G01K 7/02; G01K 1/14; G01N 19/00; G01N 33/30; G01N 19/02  
See application file for complete search history.

(56) References Cited

U.S. PATENT DOCUMENTS

| | | | |
|---|---|---|---|
| 3,045,471 | A | 7/1962 | Chapman et al. |
| 5,377,525 | A | 1/1995 | Hutchinson et al. |
| 8,151,625 | B2 | 4/2012 | Ebrecht |
| 2008/0202204 | A1 | 8/2008 | Domeier |
| 2009/0320555 | A1 | 12/2009 | Ebrecht |
| 2012/0048008 | A1 | 3/2012 | Pindiprolu et al. |

FOREIGN PATENT DOCUMENTS

| | | | | |
|---|---|---|---|---|
| JP | 2017096845 A | * | 6/2017 | ............ G01N 19/02 |
| KR | 10-2004-0083875 | | 10/2004 | |

OTHER PUBLICATIONS

International Search Report and Written Opinion from corresponding PCT Appln. No. PCT/US21/72931, dated Mar. 18, 2022.

* cited by examiner

*Primary Examiner* — Herbert K Roberts  
*Assistant Examiner* — Anthony W Megna Fuentes  
(74) *Attorney, Agent, or Firm* — Grossman, Tucker, Perreault & Pfleger, PLLC

(57) ABSTRACT

A device and method for measuring temperature during tribological examination of sample materials. More specifically, the device includes a sample holder that provides for surface temperature measurement for sample materials undergoing tribological testing.

12 Claims, 3 Drawing Sheets

DEVICE AND METHOD TO MEASURE TEMPERATURE DURING TRIBOLOGICAL EXAMINATION OF MATERIALS

FIELD

The present invention relates to a device and method for measuring temperature during tribological examination of sample materials. More specifically, the device includes a sample holder that provides for surface temperature measurement for sample materials undergoing tribological testing.

BACKGROUND

Test devices are reported for carrying out tribological examination of sample materials. Accordingly, the frictional properties between two bodies, which may be understood as frictional partners, are examined, as well as the properties of a lubricant that may be applied between two such partners. A force is applied to the frictional partners that are to be examined and the frictional force resulting from relative movement can then be determined.

It is therefore recognized that for tribological measurements of friction between materials, test devices may be utilized in which a first test body is moved relative to a second test body under a prespecified normal force load. The first test body may be connected to a corresponding movement device that can provide an oscillating or even rotational movement. The second test body is mounted in such a way that the force that is required to hold the second test body during the movement is acquired.

Test devices have since been developed where the test force between the frictional partners that are to be examined are configured such that disturbing vibrations do not arise, so that a relatively more precise determination of the frictional values can be achieved.

Reference is made to U.S. Pat. No. 8,151,625 entitled Test Device for Tribological Examination of Materials. The test device therein is described as suitable for the tribological examination of materials, including at least one first test body that has a first test surface; a drive unit for the at least one first test body that is driven in oscillating fashion and at least one second test body being arranged on a machine bed. A measurement device is provided for measuring forces that act on the one hand essentially parallel to the direction of an oscillating introduction of force of the drive unit of the at least one second test body and on the other hand for acquiring a test force that acts between the at least one first test body and the at least one second test body. A load regulating device is also provided that regulates the test force acting between the first and second test bodies, the test force being applied to the test bodies with the aid of a bearing of the drive unit being mechanically decoupled from the machine bed.

With respect to such test devices for tribological examination, a need remains for a device and method for measuring temperature during tribological examination of sample materials. More specifically, a device that includes a sample holder that provides for surface temperature measurement for the sample materials undergoing tribological testing.

SUMMARY

A sample holder for a test body for a tribological testing device comprising a base portion having a first recessed area for placement of a test body and a hollow support engaged to the base portion having a first inner opening diameter ID1 that is proximate the base portion and a second inner opening diameter ID2 that is distal to the base portion, where ID1<ID2. The hollow support first and second openings are configured to contain a thermocouple that extends into the base portion to engage with a test body placed therein.

The present invention also relates to a test device for the tribological examination of materials comprising a first test body that has a first test body surface that is configured to be driven in oscillating manner and a second test body that is positioned in a sample holder. The sample holder has a base portion having a first recessed area for placement of the second test body, a hollow support engaged to the base portion having a first inner opening diameter ID1 that is proximate the base portion and a second inner opening diameter ID2 that is distal to the base portion, where ID1<ID2, wherein the hollow support first and second openings are configured to contain a thermocouple that extends into the base portion to engage with the second test body placed therein.

DETAILED DESCRIPTION

Figure 1:
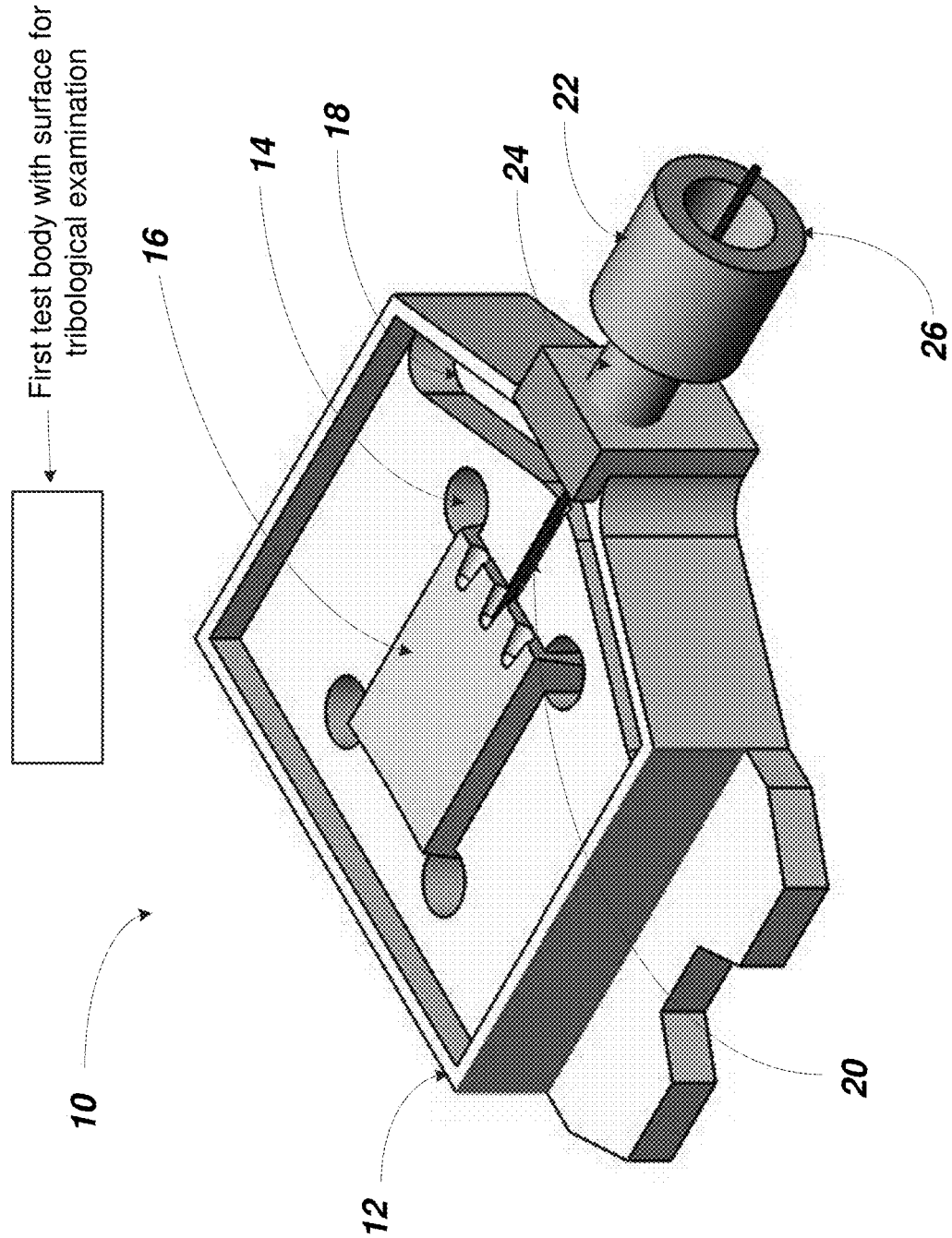
FIG. 1 illustrates in perspective view a preferred sample holder of the present invention.

Attention is directed to FIG. 1 which illustrates a preferred sample holder 10 to retain a sample material for tribological examination. The sample holder includes a base portion 12 that has a first recessed area 14 for placement of a sample material or test body 16 for tribological examination. The sample holder may also include a second recessed region 18 which may therefore serve to collect any lubricant that is being evaluated during testing. As described further herein, a thermocouple 20 is then inserted into the test body 16. The thermocouple is then routed to a temperature detection device (not shown) by passing through what may be termed a hollow support 22, preferably made of metallic material, that is engaged to the base portion 12. The support may have a first inner opening diameter ID1 at 24 that is proximate the base portion, and a second inner opening diameter ID2 at 22 that is distal to the base portion, wherein ID1<ID2.

Preferably, the support as illustrated may have a tubular shape and may therefore have a first inner opening diameter ID1 at 24 extending from the base portion 12 in the range of 0.60 mm to 0.85 mm and a second inner opening diameter ID2 at 26 in the range of 6.0 mm to 14.0 mm. ID1 and ID2 are identified in FIG. 3. The first inner diameter ID1 is preferably about 0.1 mm larger than the diameter of the thermocouple selected. The tubular support also preferably provides a length L1 (see FIG. 3) in the range of 20.0 mm to 35.0 mm. The tubular support also preferably has a wall thickness of 2.0 mm to 4.0 mm. In addition, the tubular support may have a preferred first outer diameter OD1 at 24 of 5.0 mm to 8.0 mm and a preferred second outer diameter OD2 at 26 in the range of 12.0 mm to 20.0 mm. The thermocouple 20 preferably has a diameter in the range of 0.50 mm to 0.75 mm.

Figure 2:
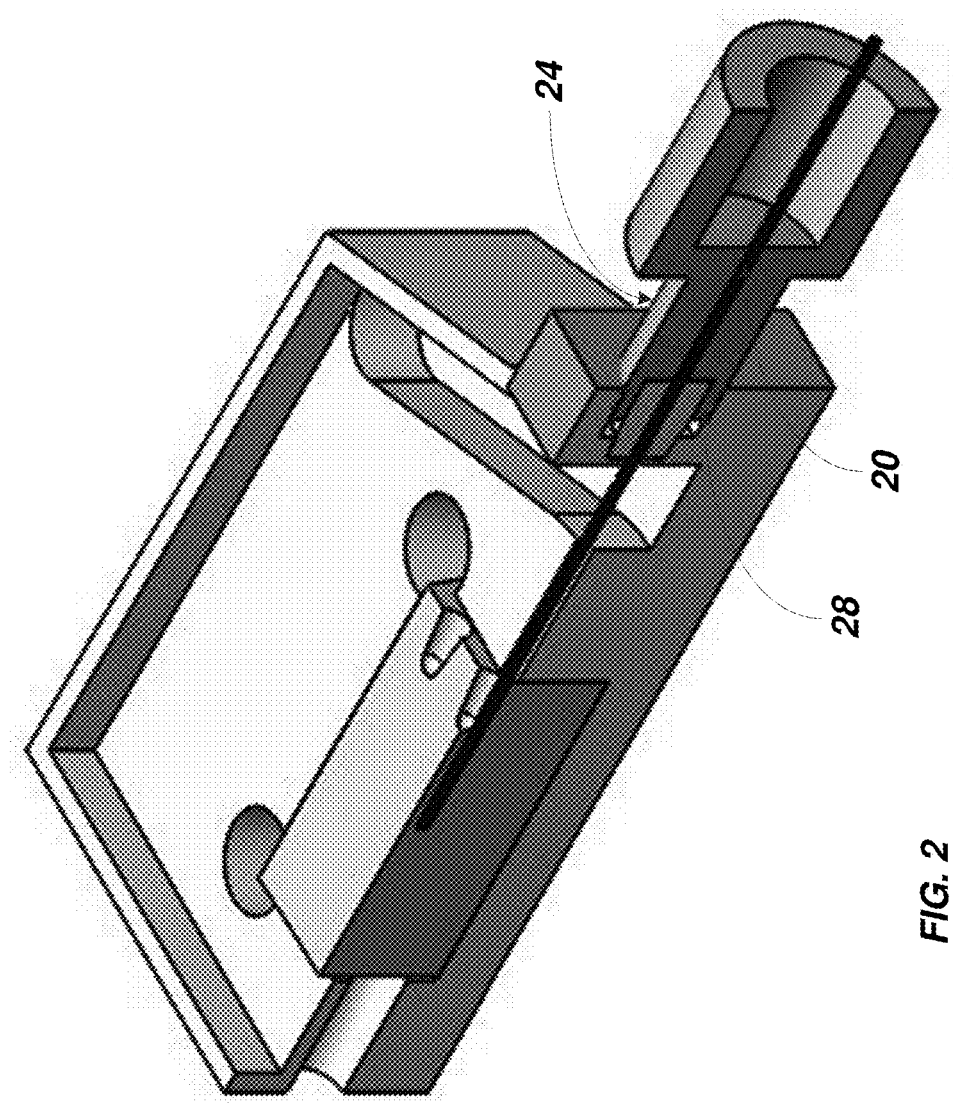
FIG. 2 illustrates a cut-away view of the preferred sample holder of FIG. 1.

As shown in FIG. 2, the portion 24 of the tubular support 22 is preferably configured such that it mechanically couples at 28 to the base portion 12 of the sample holder 10. As illustrated, and as explained further herein, a portion of the tubular support can preferably be configured with internal threads and then screwed onto the base portion.

As alluded to above, the sample material or test body 16 is now configured such that a hole is preferably drilled therein such that one may insert the thermocouple 20 into such test body. Preferably, the hole in the test body 16 is one that has a diameter in the range of 0.55-0.80 mm. As shown in cross-section in FIG. 3, the thermocouple 20 preferably extends into the test body 16 and up to about 50% of the length of the test body. In addition, the thermocouple 20 is preferably positioned so that it is present at a depth in the range of 0.25-0.75 mm from the surface 17 of the test body which is undergoing tribological examination.

Figure 3:
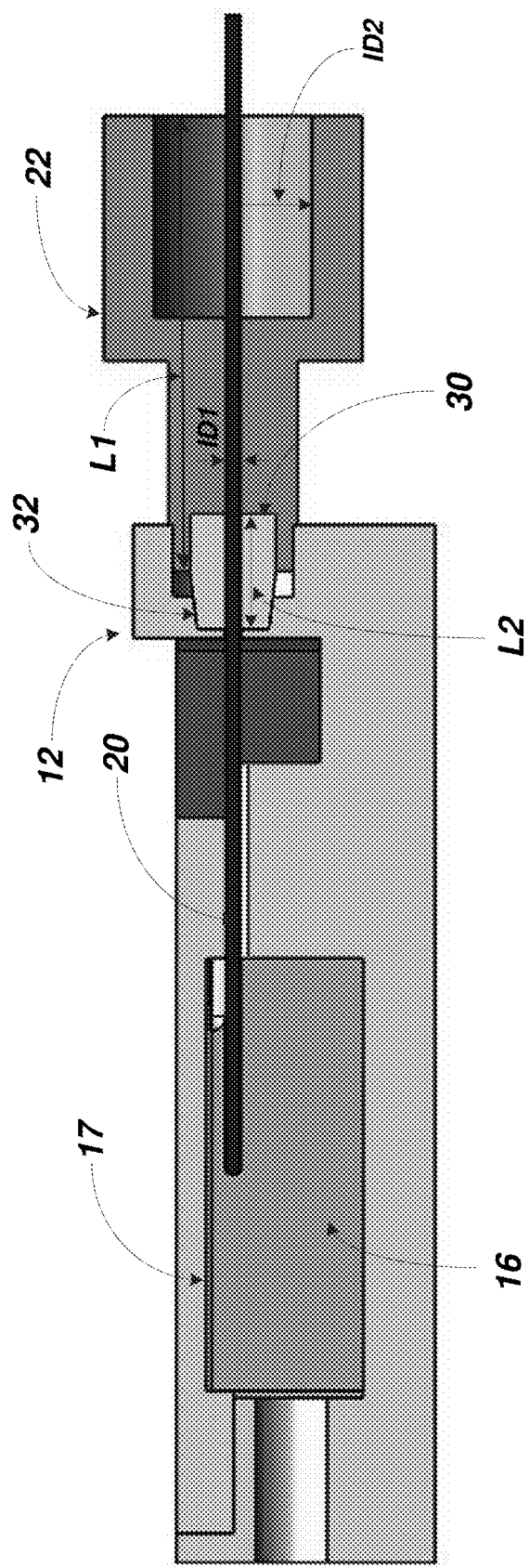
FIG. 3 illustrates a cross-sectional view of the sample holder of FIG. 1.

As also shown in FIG. 3, the sample holder may preferably include an elongated insert component 30 that allows for the thermocouple 20 to mechanically engage. The elongated insert component is positioned between the tubular support 22 and the base portion 12 and preferably includes a tapered section 32 such that when the tubular support is positively engaged with and screwed into the base portion of the sample holder, the tapered section 32 impinges upon and mechanically locks onto the thermocouple 20. The elongated insert preferably has a length L2 in the range of 5.0 mm to 10.0 mm. The insert component 30 preferably is of such material that it will deform and as noted, positively engage the thermocouple thereby holding it in place during testing. Preferred material for the insert component includes aluminum. The insert component also provides an opening for passage of the thermocouple 20, which opening preferably has an inner diameter of 0.60 mm to 0.85 mm.

The sample holder of the present invention therefore provides relatively secure fitting of a thermocouple temperature sensor to a test body undergoing tribological evaluation. By monitoring the temperature of the test body, it is contemplated that relatively more accurate tribological information can now be obtained. For example, it can be appreciated that measurement of temperature will allow for relatively more precise measurement of friction and wear between the two test bodies as well as the evaluation of the effects of lubricants. In addition the sample holder may be mounted on a heater block and the heater turned on and off such to control the test body at a predetermined test temperature.

The sample holder herein is contemplated to have particular utility in a tribological testing apparatus available from Optimol and marketed as the Optimol SRV® Basic Oscillation System. The Optimol SRV® Basic Oscillation System relies upon an electromagnetic linear drive which generates translational movement in the frequency range of 0.001 Hz to 500 Hz with strokes of 0.01 mm to 5.0 mm oscillation. The sample holder herein therefore provides the ability monitor the temperature of the test body that is being evaluated in such tribological testing unit, and for which one can apply a sinusoidal movement pattern to the test body, and measure friction forces resulting from the motion of the opposing body on the test body, along with the calculation and recording of friction coefficients and measurement and recording of total wear during and after the testing.

In such regard the device for tribological examination of materials is such that it includes at least one first test body that has a first test surface that is configured to be drive in oscillating manner and at least one second body that is now is positioned in a sample holder having a base portion having a first recessed area for placement of the second test body, a hollow support engaged to the base portion having a first inner opening diameter ID1 that is proximate the base portion and a second inner opening diameter ID2 that is distal to the base portion, where ID1<ID2, wherein said hollow support includes an opening configured to contain a thermocouple that extends into the base portion to engage with the second test body placed therein.

The invention claimed is:

1. A sample holder for a test body for a tribological testing device comprising: a base portion having a first recessed area for placement of a test body; a hollow support engaged to the base portion having a first inner opening diameter ID1 that is proximate the base portion and a second inner opening diameter ID2 that is distal to the base portion, where ID1<ID2, wherein said first and second opening diameters are configured to contain a thermocouple that extends into the base portion to engage with the test body placed therein; and an elongated insert positioned between the base portion and the hollow support.

2. The sample holder of claim 1, wherein said first inner opening diameter ID1 is in the range of 0.60 mm to 0.85 mm and said second inner opening diameter D2 is in the range of 6.0 mm to 14.0 mm.

3. The sample holder of claim 1, wherein said hollow support has a length L1 in the range of 20.0 mm to 35.0 mm.

4. The sample holder of claim 1, wherein said hollow support is engaged to said base portion via screw threads.

5. The sample holder of claim 1, further including a thermocouple and wherein said insert impinges upon and mechanically engages with said thermocouple.

6. The sample holder of claim 1, wherein said hollow support has a tubular shape.

7. A test device for the tribological examination of materials comprising: a first test body that has a first test body surface that is configured to be driven in oscillating manner; a second test body that is positioned in a sample holder having a base portion having a first recessed area for placement of the second test body; a hollow support engaged to the base portion having a first inner opening diameter ID1 that is proximate the base portion and a second inner opening diameter ID2 that is distal to the base portion, where ID1<ID2, wherein said hollow support includes an opening configured to contain a thermocouple that extends into the base portion to engage with the second test body placed therein; and an elongated insert positioned between the base portion and the hollow support.

8. The test device of claim 7, wherein said sample holder first inner opening diameter ID1 is in the range of 0.60 mm to 0.85 mm and said second inner opening diameter ID2 is in the range of 6.0 mm to 14.0 mm.

9. The test device of claim 7, wherein said hollow support has a length L1 in the range of 20.0 to 35.0 mm.

10. The test device of claim 7, wherein said hollow support is engaged to said base portion via screw threads.

11. The test device of claim 7, further including a thermocouple and wherein said insert impinges upon and mechanically engages with said thermocouple.

12. The test device of claim 7, wherein said hollow support has a tubular shape.

* * * * *